United States Patent [19]

Hester, Jr.

[11] 3,987,052
[45] Oct. 19, 1976

[54] 6-PHENYL-4H-S-TRIAZOLO[4,3-a][1,4] BENZODIAZEPINES
[75] Inventor: Jackson B. Hester, Jr., Kalamazoo, Mich.
[73] Assignee: The Upjohn Company, Kalamazoo, Mich.
[22] Filed: Oct. 29, 1969
[21] Appl. No.: 872,394

Related U.S. Application Data
[63] Continuation-in-part of Ser. No. 807,933, March 17, 1969, abandoned.

[52] U.S. Cl............................. 260/308 R; 71/92; 260/239.3 D; 424/269
[51] Int. Cl.²..................... C07D 487/04
[58] Field of Search ............... 260/308 R

[56] References Cited
UNITED STATES PATENTS
2,891,862  6/1959  Van Allan............ 260/304
3,422,091  1/1969  Archer et al......... 260/239

*Primary Examiner*—Alton D. Rollins
*Attorney, Agent, or Firm*—Hans L. Berneis; John Thomas Reynolds; Sidney W. Russell

[57] ABSTRACT
6-Phenyl-4H-s-triazolo[4,3-a][1,4]benzodiazepines of the formula (IV):

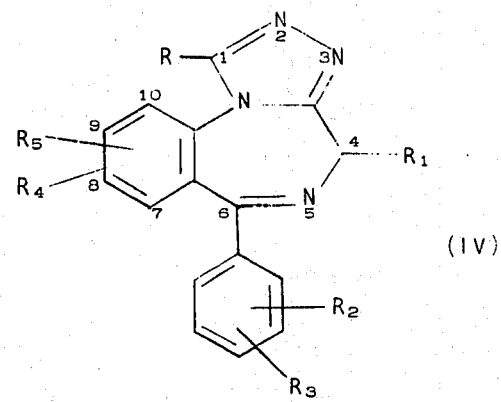

wherein R is selected from the group consisting of hydrogen, alkyl of 1 to 3 carbon atoms, inclusive, phenyl, benzyl and -COOR' in which R' is alkyl of 1 to 4 carbon atoms, inclusive; wherein $R_1$ is selected from the group consisting of hydrogen and alkyl of 1 to 3 carbon atoms, inclusive; and wherein $R_2$, $R_3$, $R_4$ and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive, are produced by condensing a 1,3-dihydro-5-phenyl-2H-1,4-benzodiazepine-2-thione of the formula (I):

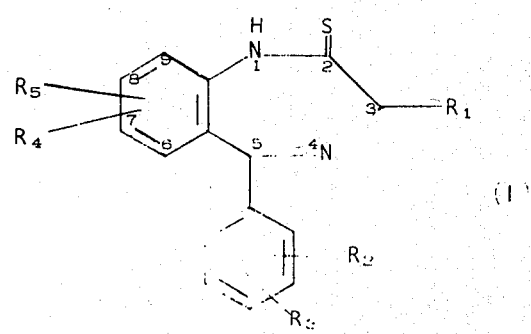

wherein $R_1$, $R_2$, $R_3$, $R_4$ and $R_5$ are defined as above, with an organic acid hydrazide of the formula:

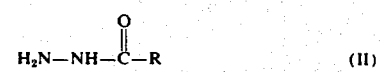

wherein R is defined as above.

The new products of formula IV including their pharmacologically acceptable acid addition salts are useful as sedatives, tranquilizers and muscle relaxants in mammals and birds.

15 Claims, No Drawings

6-PHENYL-4H-S-TRIAZOLO[4,3-A][1,4]BENZODIAZEPINES

CROSS REFERENCE TO RELATED APPLICATION

This application is a continuation-in-part of application Ser. No. 807,933, filed Mar. 17, 1969 and now abandoned.

BACKGROUND OF THE INVENTION

1. FIELD OF THE INVENTION

This invention is directed to new organic compounds and is particularly concerned with novel 6-phenyl-4H-s-triazolo-[4,3-a][1,4]benzodiazepines and a process for the production thereof.

The novel compounds and the process of production therefor can be illustratively represented as follows:

wherein R is selected from the group consisting of hydrogen, alkyl of 1 to 3 carbon atoms, inclusive, phenyl, benzyl and -COOR' in which R' is alkyl of 1 to 4 carbon atoms, inclusive; wherein $R_1$ is selected from the group consisting of hydrogen and alkyl of 1 to 3 carbon atoms, inclusive; and wherein $R_2$, $R_3$, $R_4$ and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive.

The process of this invention comprises: condensing a 1,3-dihydro-5-phenyl-2H-1,4-benzodiazepine-2-thione of formula I in an organic solvent, e.g., a loweralkanol of 1 to 4 carbon atoms, inclusive, or cyclohexanol with an acid hydrazide II, at a temperature between 60° and 120° C. to give a mixture containing the corresponding 2-(2-acylhydrazino)-5-phenyl-3H-1,4-benzodiazepine of formula III and the corresponding 6-phenyl-4H-s-triazolo-[4,3-a][1,4]benzodiazepine (IV).

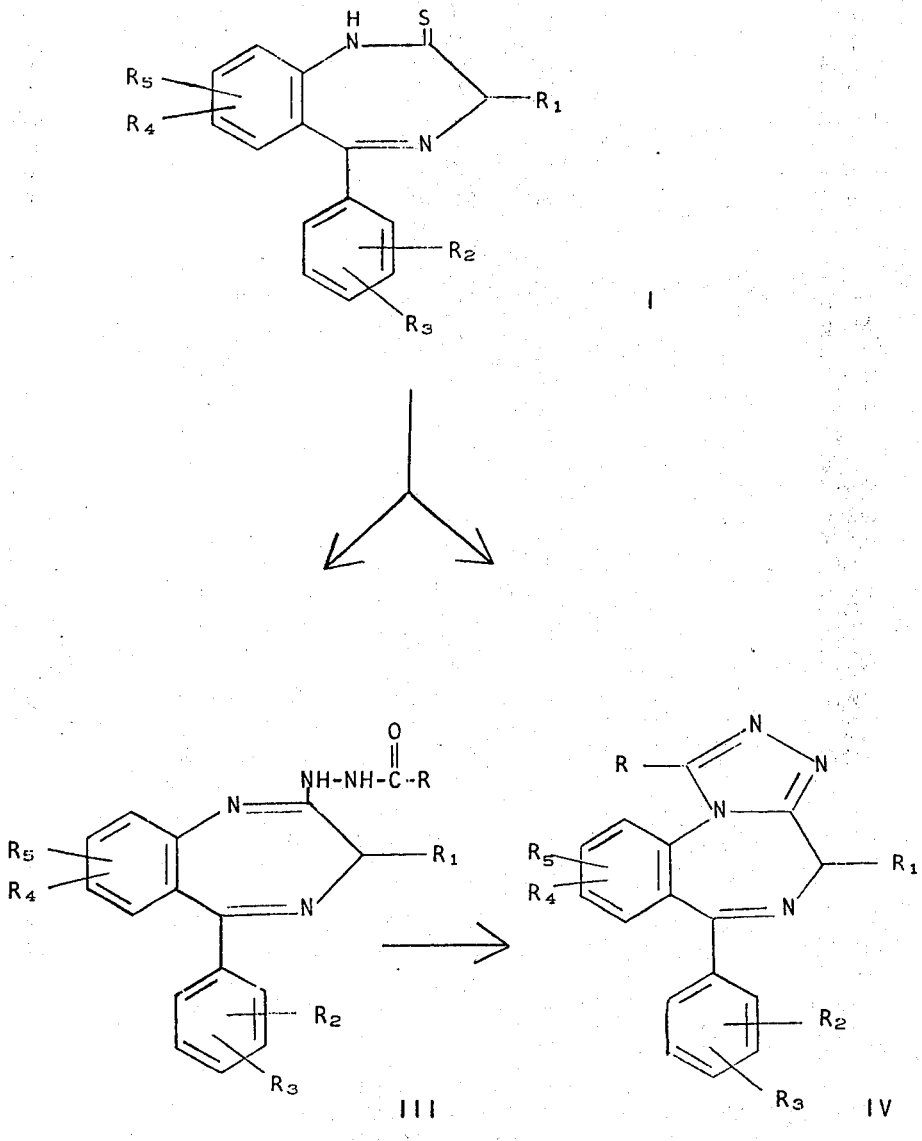

Under vigorous conditions IV is obtainable predominately. The partially condensed compound of formula III can be separated from IV by conventional methods such as extraction, chromatography, crystallization and the like, and can be converted to the corresponding triazolo-[4,3-a][1,4]benzodiazepine (IV) by heating it up to and above the melting point. Alternatively, the first obtained mixture of III and IV may be heated above the melting point to convert the partially condensed compound (III) to compound (IV).

DESCRIPTION OF THE PREFERRED EMBODIMENT

Lower alkyl groups of 1 to 3 carbon atoms, inclusive, are exemplified by methyl, ethyl, propyl and isopropyl.

Alkyl of 1 to 4 carbon atoms includes the above radicals as well as butyl and isomers thereof.

The carbon chain moiety of alkoxy, alkylthio, alkylsulfinyl, alkylsulfonyl, dialkylamino which is of 1 to 3 carbon atoms inclusive, is defined as lower-alkyl of 1 to 3 carbon atoms, inclusive, above.

The alkanoylamino group of 1 to 3 carbon atoms consists of formamido

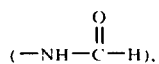

acetamido and propionamido.

The term halogen includes fluorine, chlorine, bromine and iodine.

The novel compounds of the formula IV including acid addition salts thereof have sedative, tranquilizing and muscle relaxant effects in mammals and birds.

The acid addition salts of compounds of formula IV contemplated in this invention, are the hydrochlorides, hydrobromides, hydroiodides, sulfates, phosphates, cyclohexanesulfamates, methanesulfonates and the like, prepared by reacting a compound of formula IV with the stoichiometrically calculated amount of the selected pharmacologically acceptable acid.

Sedative effects of 8-chloro-1-methyl-6-phenyl-4H-s-triazolo-[4,3-a][1,4]benzodiazepine are shown by the following tests in mice:

Chimney test: [Med. Exp. 4, 145 (1961)]: The effective intraperitoneal dosage for 50% of mice ($ED_{50}$) is 0.09 mg./kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish. The $ED_{50}$ (intraperitoneal administration) in this test was 0.15 mg./kg.; the oral $ED_{50}$ is 0.045 mg./kg.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal administration) is 0.20 mg./kg.; the $ED_{50}$ (oral administration) is 0.9 mg.kg.

Nicotine antagonism test: Mice in a group of 6 are injected with the test compound (8-chloro-1-methyl-6-phenyl-4H-s-triazolo[4,3-a][1,4]benzodiazepine). Thirty minutes later the mice including control (untreated) mice are injected with nicotine salicylate (2 mg./kg.). The control mice show overstimulation, i.e., (1) running convulsions followed by (2) tonic extensor fits; followed by (3) death. An intraperitoneal dosage of 0.1 mg./kg. of the test compound protected 50% of the mice against (2) and (3) ($ED_{50}$); the oral $ED_{50}$ is 0.04 mg./kg.

Antagonism to strychnine (as sulfate): The effective dosage $ED_{50}$ of 8-chloro-1-methyl-6-phenyl-4H-s-triazolo[4,3-a][1,4]benzodiazepine is 1 mg./kg. orally in mice. The test consists in orally administering into groups of 6 mice the test compound, 8-chloro-1-methyl-6-phenyl-4H-s-triazolo[4,3-a][1,4]benzodiazepine, and 30 minutes later 3 mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice.

The following compounds have (by intraperitoneal injection) $ED_{50}$ as shown in the table below.

| COMPOUND | $ED_{50}$ (in mg./kg.) | | | |
|---|---|---|---|---|
| | Ch | D | P | Ni |
| 8-chloro-1-methyl-6-(2,6-difluorophenyl)-4H-s-triazolo[4,3-a][1,4]benzodiazepine | 0.009 | 0.016 | 0.020 | 0.018 |
| 8-chloro-1-ethyl-6-phenyl-4H-s-triazolo-[4,3-a][1,4]benzodiazepine | 0.8 | 0.9 | 0.9 | 0.2 |
| 8-chloro-6-phenyl-4H-s-triazolo[4,3-a][1,4]-benzodiazepine | 0.25 | 0.4 | 0.7 | 0.08 |
| 8-trifluoromethyl-1-methyl-6-phenyl-4H-s-triazolo[4,3-a][1,4]-benzodiazepine | 0.16 | 0.16 | 0.22 | 0.08 |
| 8-chloro-1-methyl-6-(o-chlorophenyl)-4H-s-triazolo[4,3-a][1,4]-benzodiazepine | 0.05 | 0.028 | 0.045 | 0.008 |
| 8-chloro-1-methyl-6-(o-fluorophenyl)-4H-s-triazolo[4,3-a][1,4]-benzodiazepine | 0.056 | 0.016 | 0.028 | 0.009 |

Ch = chimney test
D = dish test
P = pedestal test
Ni = [nicotine antagonism (3) test The pharmaceutical forms contemplated by this invention include pharmaceutical compositions suited for oral, parenteral and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring and flavoring agents may be added.

For mammals and birds food premixes, with starch, oatmeal, dried fishmeat, fishmeal, flour and the like can be prepared.

As tranquilizer the compounds of formula IV can be used in dosages of 0.01 mg.–2.0 mg./kg. in oral or injectable preparations as described above, to alleviate tension and anxiety in mammals, or birds, such as e.g., occurs when animals are in travel.

Other acid addition salts of the compounds of formula IV can be made such as the fluosilicic acid addition salts which are useful mothproofing compounds or the trichloroacetates useful as herbicides against Johnson grass, Bermuda grass, yellow foxtail and green foxtail, and quack grass.

The starting materials of formula I of this invention, substituted or unsubstituted 1,3-dihydro-5-phenyl-2H-1,4-benzodiazepine-2-thiones, are described by G. A. Archer and L. H. Sternbach [J. Org. Chem. 29, 231 (1964) and U.S. Pat. No. 3,422,091]. These compounds (I) are made by the reaction of the known substituted or unsubstituted 1,3-dihydro-5-phenyl-2H-1,4-benzodiazepin-2-ones by heating with phosphorus pentasulfide in pyridine for about 45 minutes (Archer et al., ibid.). The following compounds of formula I are representative starting materials:

1,3-dihydro-5-phenyl-2H-1,4-benzodiazepine-2-thione;
6-chloro-1,3-dihydro-5-(m-bromophenyl)-2H-1,4-benzodiazepine2-thione;
7-chloro-1,3-dihydro-5-phenyl-2H-1,4-benzodiazepine-2-thione;
8-chloro-1,3-dihydro-5-phenyl-2H-1,4-benzodiazepine-2-thione;
7-bromo-1,3-dihydro-5-phenyl-2H-1,4-benzodiazepine-2-thione;
7-chloro-1,3-dihydro-5-(3,4-dimethylphenyl)-2H-1,4-benzodiazepine-2-thione;
1,3-dihydro-5-(2-methyl-4-methoxyphenyl)2H-1,4-benzodiazepine-2-thione;
9-bromo-1,3-dihydro-5-phenyl-2H-1,4-benzodiazepine-2-thione;
7-methyl-1,3-dihydro-5-phenyl-2H-1,4-benzodiazepine-2-thione;
7-nitro-1,3-dihydro-5-phenyl-2H-1,4-benzodiazepine-2-thione;
7-fluoro-1,3-dihydro-5-phenyl-2H-1,4-benzodiazepine-2-thione;
7-trifluoromethyl-1,3-dihydro-5-phenyl-2H-1,4-benzodiazepine-2-thione;
9-trifluoromethyl-1,3-dihydro-5-[p-(propionylamino)-phenyl]-2H-1,4-benzodiazepine-2-thione;
7-cyano-1,3-dihydro-5-phenyl-2H-1,4-benzodiazepine-2-thione;
8-cyano-1,3-dihydro-5-[p-(trifluoromethyl)phenyl]-2H-1,4-benzodiazepine-2-thione;
7-chloro-1,3-dihydro-5-(o-chlorophenyl)-2H-1,4-benzodiazepine-2-thione;
6-ethylthio-1,3-dihydro-5-(o-bromophenyl)-2H-1,4-benzodiazepine-2-thione;
6,8-dichloro-1,3-dihydro-5-(o-fluorophenyl)-2H-1,4-benzodiazepine-2-thione;
8-propoxy-7-bromo-1,3-dihydro-5-[m-(ethylsulfinyl)-phenyl]-2H-1,4-benzodiazepine-2-thione;
9-diisopropylamino-7-methyl-1,3-dihydro-5-[m-(propylsulfonyl)-phenyl]-2H-1,4-benzodiazepine-2-thione;
7-bromo-1,3-dihydro-5-(o-fluorophenyl)-2H-1,4-benzodiazepine-2-thione;
3-methyl-1,3-dihydro-5-(o-fluorophenyl)-2H-1,4-benzodiazepine-2-thione;
7-fluoro-1,3-dihydro-5-(o-fluorophenyl)-2H-1,4-benzodiazepine-2-thione;
3-methyl-1,3-dihydro-5-(p-fluorophenyl)-2H-1,4-benzodiazepine-2-thione;
7-nitro-1,3-dihydro-5-(o-chlorophenyl)-2H-1,4-benzodiazepine-2-thione;
8-nitro-1,3-dihydro-5-(o-chlorophenyl)-2H-1,4-benzodiazepine-2-thione;
7-bromo-1,3-dihydro-5-(o-bromophenyl)-2H-1,4-benzodiazepine-2-thione;
7-methylsulfinyl-1,3-dihydro-5-(o-fluorophenyl)-2H-1,4-benzodiazepine-2-thione;
7-methyl-1,3-dihydro-5-(o-chlorophenyl)-2H-1,4-benzodiazepine-2-thione;
7-methylthio-1,3-dihydro-5-phenyl-2H-1,4-benzodiazepine-2-thione;
7-cyano-1,3-dihydro-5(o-chlorophenyl)-2H-2,4-benzodiazepine-2-thione;
3,6,8-trimethyl-1,3-dihydro-5-(o-chlorophenyl)-2H-1,4-benzodiazepine-2-thione;
9-propylsulfonyl-7-methyl-1,3-dihydro-5-phenyl-2H-1,4-benzodiazepine-2-thione;
7-trifluoromethyl-1,3-dihydro-5-(o-chlorophenyl)-2H-1,4-benzodiazepine-2-thione;
7-dimethylamino-1,3-dihydro-5-phenyl-2H-1,4-benzodiazepine-2-thione;
7-fluoro-1,3-dihydro-5-(o-chlorophenyl)-2H-1,4-benzodiazepine-2-thione;
7,8-dicyano-1,3-dihydro-5-[p-(methylsulfonyl)-phenyl]-2H-1,4-benzodiazepine-2-thione;
6,9-dichloro-1,3-dihydro-5-(p-isopropylphenyl)-2H-1,4-benzodiazepine-2-thione;
6,8-diethyl-1,3-dihydro-5-(m-ethylphenyl)-2H-1,4-benzodiazepine-2-thione;
6-nitro-1,3-dihydro-5-(o-cyanophenyl)-2H-1,4-benzodiazepine-2-thione;
7,9-bis(dipropylamino)-1,3-dihydro-5-(o-nitrophenyl)-2H-1,4-benzodiazepine-2-thione;
9-acetylamino-1,3-dihydro-5-(p-cyanophenyl)-2H-1,4-benzodiazepine-2-thione; and the like.

In carrying out the process of the invention, a selected 1,3-dihydro-5-phenyl-2H-1,4-benzodiazepine-2-thione (I) in an inert organic solvent, preferably in a lower-alkanol, e.g., methanol, ethanol, 1-propanol, 2-propanol, 1-butanol, 2-butanol or the like is heated to between 60°–120° C., preferably to the reflux temperature of the mixture, with the selected acid hydrazide $NH_2$-NH-COR (II) defined as above. In the preferred embodiment of this invention the acid hydrazide is used in excess such as from 2 to 5 times the theoretically required amount, but the reaction is operative with smaller or larger amounts. The reaction period is between 1 and 48 hours. At the termination of the reaction the reaction mixture can be evaporated to give a crude product consisting of the desired 6-phenyl-4H-s-triazolo[4,3-a][1,4]benzodiazepine (IV) and the partially condensed compound, a 2-(2-acylhydrazino)-5-phenyl-3H-1,4-benzodiazepine (III), which can be separated from each other, usually by their different solubility in an organic solvent, e.g., methylene chloride, chloroform, carbon tetrachloride, ethyl acetate, mixtures thereof and the like. The compound III after separation can be converted to compound IV by heating it above the melting point of compound IV for 1 to 10 minutes. In a more simple manner the crude mixture of compounds III and IV is heated to 200°–275° C., thereby converting all of compound III to compound IV. The crude compound IV is then purified by standard methods, e.g., chromatography or recrystallization from solvents such as ethyl acetate, methylene chloride, chloroform, acetonitrile or the like.

The following examples are illustrative of the processes and products of the present invention, but are not to be construed as limiting.

PREPARATION 1

1,3-Dihydro-7-chloro-5-(2,6-difluorophenyl)-2H-1,4-benzodiazepin-2-one

A. 2-Acetamido-5-chloro-2',6'-difluorobenzophenone

To a solution of 114 g. (1.0 mole) of m-difluorobenzene in 800 ml. of dry tetrahydrofuran cooled to −50° C. and maintained under a nitrogen atmosphere was added, with stirring, 320 ml. of an n-heptane solution of n-butyl lithium containing 1.0 mole of the latter. The addition was carried out during 50 minutes and was followed by stirring 2 hours more at −50° C. The cold solution was then added with stirring during 50 minutes to a solution of 187.8 g. (0.97 mole) of 6-chloro-2-methyl-4H-3,1-benzoxazin-4-one [J. Am. Chem. Soc. 70, 2423 (1948)] in 1400 ml. of benzene and 1000 ml. of tetrahydrofuran at 25° C. The mixture was stirred under a nitrogen atmosphere for 20 hours, at which time 1000 ml. of 2N hydrochloric acid was added. The aqueous layer was separated and discarded. The organic layer was filtered to remove suspended solid material and the filtrate was washed with cold, dilute aqueous sodium hydroxide solution. Three layers were present, a light colored aqueous phase, a dark brown aqueous phase, and an organic phase. The organic phase, after being dried with anhydrous sodium sulfate, was concentrated to give 101 g. of a semi-solid which was then extracted with 2100 ml. of hot Skellysolve B hexanes. Evaporation of the extract gave 39.9 g. of crude product of melting point 106°–116° C. Recrystallization of this material from Skellysolve B gave purified 2-acetamido-5-chloro-2',6'-difluorobenzophenone of melting point 118°–120° C.

Anal. Calcd. for $C_{15}H_{10}ClF_2NO_2$: C, 58.17; H, 3.25; Cl, 11.45; F, 12.27; N, 4.52. Found: C, 58.11; H, 3.38; Cl, 11.53; F, 12.24; N, 4.20.

B. 2-Amino-5-chloro-2',6'-difluorobenzophenone

A suspension of 4.2 g. (0.014 mole) of 2-acetamido-5-chloro-2',6'-difluorobenzophenone in 350 ml. of concentrated hydrochloric acid and 350 ml. of water was heated on a steam bath with stirring and in a nitrogen atmosphere until complete solution resulted. The solution was cooled and basified with 50% aqueous sodium hydroxide solution. The resulting solid was removed by extraction with methylene chloride. The extract was dried with anhydrous sodium sulfate and evaporated to dryness. The residue was recrystallized from cyclohexane to give 2.4 g. of 2-amino-5-chloro-2',6'-difluorobenzophenone of melting point 103°–105° C.

Anal. Calcd. for $C_{13}H_{10}ClF_2NO$: C, 58.33; H, 3.01; Cl, 13.24; F, 14.20; N, 5.23. Found: C, 58.33; H, 3.29; Cl, 13.31; F, 14.87; N, 5.14.

C. 2-(2-Bromoacetamido)-5-chloro-2',6'-difluorobenzophenone

To a solution of 2.7 g. (0.01 mole) of 2-amino-5-chloro-2',6'-difluorobenzophenone in 100 ml. of benzene, through which a rapid stream of nitrogen was passed, was added 3.03 g. (0.015 mole) of bromoacetyl bromide. A precipitate formed soon after addition was complete. The benzene was removed by evaporation and the solid residue was recrystallized from cyclohexane to yield 3.4 g. of 2-(2-bromoacetamido)-5-chloro-2',6'-difluorobenzophenone of melting point 146°–147.5° C.

Anal. Calcd. for $C_{15}H_9BrClF_2NO_2$: C, 46.36; H, 2.33; Br, 20.56; Cl, 9.12; F, 9.78; N, 3.60. Found: C, 46.46; H, 2.48; Br, 20.68; Cl, 9.21; F, 9.49; N, 3.82. methylene

D. 2-(2-Aminoacetamido)-5-chloro-2',6'-difluorobenzophenone

Liquid ammonia (350 ml.) was added to a solution of 26 g. (0.067 mole) of 2-(2-bromoacetamido)-5-chloro-2',6'-difluorobenzophenone in 350 ml. of methylene chloride. The solution was stirred under reflux for 5 hours and was then stirred for about 16 hours while excess ammonia evaporated. The methlene chloride solution was filtered to remove solid material and was then evaporated to dryness. The residue was recrystallized from 2 l. of cyclohexane to obtain 19.4 g. of 2-(2-aminoacetamido)-5-chloro-2',6'-difluorobenzophenone of melting point 133°–135° C.

Anal. Calcd. for $C_{15}H_{11}ClF_2N_2O_2$: C, 55.48; H, 3.42; Cl, 10.92; F, 11.70; N, 8.63. Found: C, 56.69; H, 3.99; Cl, 11.19; F, 11.06; N, 8.34.

E. 1,3-Dihydro-7-chloro-5-(2,6-difluorophenyl)-2H-1,4-benzodiazepin-2-one

A solution of 21.0 g. (0.065 mole) of 2-(2-aminoacetamido)-5-chloro-2',6'-difluorobenzophenone in 300 ml. of pyridine was heated under reflux in a nitrogen atmosphere for 18 hours. The pyridine was removed by evaporation. The residue after being washed with Skellysolve B hexanes was recrystallized, first from ethyl acetate-Skellysolve B hexanes and then from ethyl acetate. There was thus obtained a first crop (11.7 g.; melting point 248°–249° C.) and a second crop (2.3 g.; melting point 244°–246° C.) of 1,3-dihydro-7-chloro-5-(2,6-difluorophenyl)-2H-1,4-benzodiazepin-2-one.

Anal. Calcd. for $C_{15}H_9ClF_2N_2O$: C, 58.74; H, 2.96; Cl, 11.56; F, 12.39; N, 9.14. Found: C, 58.89; H, 2.78; Cl, 11.39; F, 11.72; N, 8.95.

This material was found to contain 1.9% ethyl acetate of solvation. Recrystallization of the solvated material from ethanol provides unsolvated 1,3-dihydro-7-chloro-5-(2,6-difluorophenyl)-2H-1,4-benzodiazepin-2-one.

PREPARATION 2

1,3-Dihydro-7-chloro-5-(2,6-difluorophenyl)-2H-1,4-benzodiazepine-2-thione

A solution of 7.65 g. (0.025 mole) of 1,3-dihydro-7-chloro-5-(2,6-difluorophenyl)-2H-1,4-benzodiazepin-2-one in 500 ml. of pyridine was treated with 5.55 g. (0.025 mole) of phosphorus pentasulfide and heated under reflux in a nitrogen atmosphere for two hours. The pyridine (350 ml.) was removed in vacuo and the thus-produced residue was poured onto crushed ice. The aqueous phase was extracted with methylene chloride and then discarded. The extract was washed successively with three 200-ml. portions of water and 100 ml. of brine, and dried over anhydrous sodium sulfate. Removal of the solvent gave 7.0 g. of solid which was recrystallized from ethanol-water, to give in 2 crops 6.8 g. of crude material which, after recrystallization from ethanol-water, gave pure 1,3-dihydro-7-chloro-5-(2,6-difluorophenyl)-2H-1,4-benzodiazepine-2-thione of melting point 222.5°–224° C.

Anal. Calcd. for $C_{15}H_9ClF_2N_2S$: C, 55.82; H, 2.81; Cl, 10.98; F, 11.77; N, 8.68; S, 9.93. Found: C, 56.13; H, 2.68; Cl, 11.13; F, 11.69; N, 8.40; S, 9.84.

PREPARATION 3

1,3-Dihydro-7-(trifluoromethyl)-5-phenyl-2H-1,4-benzodiazepine-2-thione

A stirred mixture of 1,3-dihydro-7-trifluoromethyl-5-phenyl-2H-1,4-benzodiazepin-2-one (89.7 g.; 0.294 mole), dry pyridine (2300 ml.) and phosphorus pentasulfide (72.4 g.; 0.323 mole) was refluxed under nitrogen for 30 minutes, cooled and concentrated in vacuo. A suspension of the residue in ice water was extracted with methylene chloride. The extract was dried over anhydrous potassium carbonate and concentrated. The residue was crystallized from methylene chloride-ethanol to give 43.2 g. of melting point 228.5°–229° C. (dec.) and 17.8 g. of melting point 229°–230° C. (dec.) (64.5%) of 1,3-dihydro-7-(trifluoromethyl)-5-phenyl-2H-1,4-benzodiazepine-2-thione. The analytical sample prepared by recrystallization from methylene chloride-ethanol had a melting point of 223.5° C. (dec.).

Anal. Calcd. for $C_{16}H_{11}F_3N_2S$:

C, 60.00; H, 3.46; F, 17.79; N, 8.75; S, 10.01.

C, 59.85; H, 3.73; F, 17.83; N, 8.42; S, 10.26

EXAMPLE 1

8-Chloro-1-methyl-6-phenyl-4H-s-triazolo[4,3-a]-[1,4]benzodiazepine

A. 2-(2-Acetylhydrazino)-7-chloro-5-phenyl-3H-1,4-benzodiazepine

A mixture of 2.0 g. (0.0070 mole) of 7-chloro-1,3-dihydro-5-phenyl-2H-1,4-benzodiazepine-2-thione, 1.55 g. (0.021 mole) of acetic acid hydrazide and 70 ml. of absolute ethanol was refluxed for 24 hours with a slow stream of nitrogen bubbling through the mixture. The mixture was then concentrated to give a residue. A suspension of this residue in methylene chloride was filtered. Concentration of the filtrate and crystallization of the residue from ethyl acetate gave 0.65 g. of 2-(2-acetylhydrazino)-7-chloro-5-phenyl-3H-1,4-benzodiazepine of melting point 196°–197° C. (dec.). The analytical sample of melting point 199°–200° C. (dec.) was prepared by recrystallizing some of this material from methylene chloride-ethyl acetate. The ultraviolet spectrum (ethanol) had end absorption λ max. 262 ($\epsilon$=26,900) and 336 ($\epsilon$= 1,950) and an inflection at 210 m$\mu$ ($\epsilon$ = 28,200).

Anal. Calcd. for $C_{17}H_{15}ClN_4O$:

C, 62.48; H, 4.63; Cl, 10.85; N,17.15.

Found: C, 62.20; H, 4.63; Cl, 11.13; N, 16.99.

Crystallization of the solid from the methylene chloride filtrate gave 0.73 g. of a mixture of 2-(2-acetylhydrazino)-7-chloro-5-phenyl-3H-1,4-benzodiazepine and 8-chloro-1-methyl-6-phenyl-4H-s-triazolo[4,3-a][1,4]benzodiazepine.

B. 8-Chloro-1-methyl-6-phenyl-4H-s-triazolo[4,3-a][1,4]-benzodiazepine

A sample of 2-(2-acetylhydrazino)-7-chloro-5-phenyl-3H-1,4-benzodiazepine was heated under nitrogen at 250° C. for a few minutes. Crystallization of the cooled melt from ethyl acetate gave 8-chloro-1-methyl-6-phenyl-4H-s-triazolo[4,3-a]-[1,4]benzodiazepine of melting point 228°–228.5° C. The ultraviolet spectrum (ethanol) had end absorption λ max. 222 ($\epsilon$= 40,250) and inflections 245 ($\epsilon$= 15,350), 265 ($\epsilon$ = 6,250) and 290 m$\mu$($\epsilon$ = 2,850).

Anal. Calcd. for $C_{17}H_{13}ClN_4$:

C, 66.13; H, 4.24; Cl, 11.48; N, 18.15.

Found: C, 66.05; H, 4.13; Cl, 11.34; N, 18.00.

EXAMPLE 2

8-Chloro-1-methyl-6-phenyl-4H-s-triazolo[4,3-a]-[1,4]benzodiazepine

In the manner given in Example 1A, 50 g. of 7-chloro-1,3-dihydro-5-phenyl-2H-1,4-benzodiazepine-2-thione was heated with 38.9 g. of acetic acid hydrazide in 1760 ml. of absolute ethanol for a period of 24 hours. The reaction mixture was then cooled and concentrated to give a residue. The residue was treated with water and the aqueous suspension filtered. The solids remaining on the filter were dissolved in methylene chloride, the solution was dried over anhydrous potassium carbonate, evaporated and the residue recrystallized once from ethyl acetate. The material thus obtained (in two crops: 30.7 g. of melting point 225°–226.5° C. and 4.13 g. of melting point 222°–223° C.) was melted under nitrogen in an oil bath maintained at 250° C., cooled and crystallized from ethyl acetate to give 25.5 g. (47.7%) of 8-chloro-1-methyl-6-phenyl-4H-s-triazolo[4,3-a][1,4]benzodiazepine of melting point 227.5°–228.5° C. EXAMPLE 3 8-Chloro-1-methyl-6-(2,6-difluorophenyl)-4H-s-triazolo[4,3-a][1,4]benzodiazepine A solution of 6.0 g. (0.0186 mole) of 1,3-dihydro-7-chloro-5-(2,6-difluorophenyl)-2H-1,4-benzodiazepine-2-thione and 4.14 g. (0.0558 mole) of acetic acid hydrazide in 250 ml. of 1-butanol was heated under reflux. During the first hour a stream of nitrogen was passed through the reaction mixture to remove the hydrogen sulfide formed. The heating was continued for 18 hours in a nitrogen atmosphere. The reaction mixture was concentrated, the residue poured into water, and extracted with methylene chloride. The organic layer was dried over anhydrous sodium sulfate. Removal of the solvent gave 6.8 g. of orange solid which was recrystallized from ethanol to give in two crops 4.5 g. (70%) of 8-chloro-1-methyl-6-(2,6-difluorophenyl)-4H-s-triazolo[4,3-a][1,4]benzodiazepine of melting point 278°–279.5° C.

Anal. Calcd. for $C_{17}H_{11}ClF_2N_4$:

C, 59.22; H, 3.22; Cl, 10.28; F, 11.02; N, 16.26.

Found: C, 59.41; H, 3.31; Cl, 10.32; F, 11.06; N, 16.18.

By heating the reaction mixture at lower temperature (replacing 1-butanol by ethanol) or for shorter periods of time, the open chain intermediate, 2-(2-acetylhydrazino)-7-chloro-5-(2,6-difluorophenyl)-3H-1,4-benzodiazepine, can be isolated. This material, recrystallized from ethanol, has a melting point of 274°–277° C.

Anal. Calcd. for $C_{17}H_{13}ClF_2N_4O$:

C, 56.28; H, 3.61; Cl, 9.77; F, 10.47; N, 15.45.

Found: C, 56.02; H, 3.49; Cl, 9.78; F, 10.62; N, 15.53.

EXAMPLE 4

8-Chloro-1-methyl-6-(o-fluorophenyl)-4H-s-triazolo-[4,3-a][1,4]benzodiazepine

A solution of 1.52 g. (0.005 mole) of 7-chloro-1,3-dihydro-5-(o-fluorophenyl)-2H-1,4-benzodiazepine-2-thione and 1.11 g. (0.015 mole) of acetic acid hydrazide in 50 ml. of 1-butanol was refluxed for 12 hours while bubbling a stream of nitrogen through the reaction mixture. The solvent was evaporated in vacuo and the residue was treated with water and methylene chloride. The phases were separated and the organic layer was dried over anhydrous sodium sulfate and concentrated to an oil. The crude oil was triturated with ethyl acetate-Skellysolve B hexanes and the resulting solid was filtered to give 1.32 g. of solid of melting point 202°–203° C. Crystallization from ethyl acetate-Skellysolve B hexanes yielded 1.13 g. (70%) of 8-chloro-1-methyl-6-(o-fluorophenyl)-4H-s-triazolo[4,3-a][1,4]benzodiazepine of melting point 203°–204° C.

Anal. Calcd. for $C_{17}H_{12}ClFN_4$:

C, 62.49; H, 3.70; Cl, 10.85; F, 5.81; N, 17.15. Found: C, 62.39; H, 3.87; Cl, 10.91; 6.03; N, 17.11.

EXAMPLE 5

1-Methyl-6-phenyl-4H-s-triazolo[4,3-a][1,4]benzodiazepine

A stirred mixture of 1,3-dihydro-5-phenyl-2H-1,4-benzodiazepine-2-thione (4.49 g.; 0.0179 mole), acetic acid hydrazide (3.98 g.; 0.0537 mole) and 1-butanol (200 ml.) was refluxed for 3.5 hours with a slow stream of nitrogen bubbling through the reaction mixture. The mixture was concentrated in vacuo and the residue was suspended in water and extracted with methylene chloride. The extract was dried over anhydrous potassium carbonate and concentrated. Crystallization of the residue from ethyl acetate gave 2.97 g. (60.6%) of 1-methyl-6-phenyl-4H-s-triazolo[4,3-a][1,4]benzodiazepine of melting point 216°–218° C. The analytical sample prepared by recrystallizing some of this material from ethyl acetate had a melting point of 230°–231° C. The ultraviolet spectrum (ethanol) had end absorption λ max. 216 ($\epsilon$= 34,550) and inflections 243 ($\epsilon$= 13,550), and 280 m$\mu$($\epsilon$= 4,300).

Anal. Calcd. for $C_{17}H_{14}N_4$: C, 74.43; H, 5.14; N, 20.43 Found: C, 74.10; H, 5.18; N, 20.05.

EXAMPLE 6

8-Chloro-1-propyl-6-phenyl-4H-s-triazolo[4,3-a][1,4]benzodiazepine

In the manner given in Example 2, 7-chloro-1,3-dihydro-5-phenyl-2H-1,4-benzodiazepine-2-thione was heated in 1-butanol with butyric acid hydrazide and the resulting product heated to 250° C. to give 8-chloro-1-propyl-6-phenyl-4H-s-triazolo[4,3-a]-[1,4]benzodiazepine of melting point 176°–176.5° C. The ultraviolet spectrum (ethanol) had end absorption λ max. 209 ($\epsilon$= 40,450) and inflections 237 ($\epsilon$= 14,900), 245 ($\epsilon$= 15,850), 270 ($\epsilon$= 5,750) and 290 m$\mu$($\epsilon$= 3,000).

Anal. Calcd. for $C_{19}H_{17}ClN_4$: C, 67.75; H, 5.09; Cl, 10.53; N, 16.63. Found: C, 67.96; H, 5.09; Cl, 10.63; N, 16.59

EXAMPLE 7

8-Chloro-1-isopropyl-6-phenyl-4H-s-triazolo[4,3-a][1,4]benzodiazepine

In the manner given in Example 2, 7-chloro-1,3-dihydro-5-phenyl-2H-1,4-benzodiazepine-2-thione is heated in ethanol with isobutyric acid hydrazide and the resulting product heated to 250° C. to give 8-chloro-1-isopropyl-6-phenyl-4H-s-triazolo-[4,3-a][1,4]benzodiazepine.

EXAMPLE 8

8-Chloro-1,6-diphenyl-4H-s-triazolo[4,3-a][1,4]-benzodiazepine

In the manner given in Example 2, 7-chloro-1,3-dihydro-5-phenyl-2H-1,4-benzodiazepine-2-thione was heated in ethanol with benzoic acid hydrazide and the resulting product heated to 250° C. to give 8-chloro-1,6-diphenyl-4H-s-triazolo[4,3-a]-[1,4]benzodiazepine of melting point 193.5°–194.5° C.

Anal. Calcd. for $C_{22}H_{15}ClN_4$: C, 71.25; H, 4.08; Cl, 9.56; N, 15.11. Found: C, 71.56; H, 4.17; Cl, 9.63; N, 15.16.

EXAMPLE 9

1-Benzyl-8-chloro-6-phenyl-4H-s-triazolo[4,3-a][1,4]benzodiazepine

A mixture of 7-chloro-1,3-dihydro-5-phenyl-2H-1,4-benzodiazepine-2-thione (5.74 g.; 0.200 mole), phenylacetic acid hydrazine (9.0 g.) and 1-butanol (200 ml.) was refluxed for 5 hours with a slow stream of nitrogen bubbling through the reaction mixture. The mixture was concentrated in vacuo, and the residue was suspended in water and stirred for one hour. The solid product was collected by filtration and dissolved in methylene chloride. The solution was dried over anhydrous potassium carbonate and concentrated. Crystallization of the residue from ethyl acetate-Skellysolve B hexanes gave 5.28 g. (68.6%) of 1-benzyl-8-chloro-6-phenyl-4H-s-triazolo[4,3-a]-[1,4]benzodiazepine of melting point 191°–192° C. The analytical sample prepared by recrystallizing some of this material from ethyl acetate-Skellysolve B hexanes had a melting point of 192.5°–193.5° C. The ultraviolet spectrum (ethanol) had end absorption λ max. 221 ($\epsilon$= 35,850) and inflections 248 ($\epsilon$= 14,550), 265 ($\epsilon$= 6,100) and 290 m$\mu$($\epsilon$= 2,300).

Anal. Calcd. for $C_{23}H_{17}ClN_4$: C, 71.77; H, 4.45; Cl, 9.21; N, 14.56. Found C, 77.77; H, 4.63; Cl, 9.32; N, 14.79.

EXAMPLE 10

8-Chloro-1-ethyl-6-phenyl-4H-s-triazolo[4,3-a][1,4]benzodiazepine

In the manner given in Example 2, 7-chloro-1,3-dihydro-5-phenyl-2H-1,4-benzodiazepine-2-thione was heated in ethanol with propionic acid hydrazide and the resulting product heated to 250° C. to give 8-chloro-1-ethyl-6-phenyl-4H-s-triazolo-[4,3-a][1,4]benzodiazepine of melting point 231.5°–232.5° C. The ultraviolet spectrum (ethanol) had end absorption λ max. 224 ($\epsilon$ = 39,250) and inflections 248 ($\epsilon$ = 15,000), 266 ($\epsilon$ = 6,900) and 290 m$\mu$($\epsilon$ = 3,250).

Anal. Calcd. for $C_{18}H_{15}ClN_4$: C, 66.97; H, 4.68; Cl, 10.99; N, 17.36. Found C, 66.73; H, 4.83; Cl, 10.92; N, 17.29.

EXAMPLE 11

1-methyl-6-phenyl-8-(trifluoromethyl)-4H-s-triazolo[4,3-a][1,4]benzodiazepine A stirred mixture of 1,3-dihydro-5-phenyl-7-(trifluoromethyl)-2H-1,4-benzodiazepine-2-thione (64.9 g.; 0.204 mole), acetic acid hydrazide (45.3 g.; 0.612 mole) and methanol (2500 ml.) was refluxed under nitrogen for 24 hours; during the first two hours nitrogen was bubbled through the refluxing mixture. The mixture was concentrated in vacuo. A suspension of the residue in water was stirred for one hour and filtered. The solid was dried at 30° C. in vacuo to give 64 g. of crude 2-(2-acetylhydrazino)-7-(trifluoromethyl)-5-phenyl-3H-1,4-benzodiazepine. This material was heated in batches of 10–20 g. at 200° C. under reduced pressure (12 mm.) until the solid had melted and bubbling had become slow. The oily product was combined and stored at 4° C. The crystalline material which resulted was collected by filtration, washed with ether and dried to give 33.4 g. of crude product. The mother liquor was chromatographed on silica gel (3 kg.) with 5% methanol-95% benzene (by volume) to give additional product. The combined product was recrystallized from wet methylene chloride-ether in two crops: 25.2 g., melting point 120.5°–127.5° C., and 12.8 g., melting point 120°–127° C. of 1-methyl-6-phenyl-8-(trifluoromethyl)-4H-s-triazolo[4,3-a][1,4]benzodiazepine hydrate. The first crop had ultraviolet spectrum (ethanol) having λ max. 219 (ε = 31,400) and inflections 247 (ε = 13,100) and 280 mμ(ε = 3,850).

Anal. Calcd. for $C_{18}H_{13}F_3N_4$: C, 63.15; H, 3.83; F, 16.65; N, 16.37. Found for hydrate: C, 59.07; H, 4.88; F, 15.90; N, 15.48; $H_2O$, 5.85. Corrected for $H_2O$: C, 62.73; H, 4.49; F, 16.90; N, 16.45.

Heating this product to 80° C. for a period of 72 hours at a pressure of 12 mm. Hg gave water-free 1-methyl-6-phenyl-8-(trifluoromethyl)-4H-s-triazolo[4,3-a][1,4]benzodiazepine.

EXAMPLE 12

1-Methyl-8-nitro-6-phenyl-4H-s-triazolo[4,3-a]-[1,4]benzodiazepine.

A stirred mixture of 1,3-dihydro-7-nitro-5-phenyl-2H-1,4-benzodiazepine-2-thione (2.97 g.; 0.01 mole), acetic acid hydrazide (2.21 g.; 0.03 mole) and 1-butanol (100 ml.) ws refluxed for 1.5 hours with a slow stream of nitrogen bubbling through the reaction mixture. The resulting mixture was concentrated in vacuo. The residue was suspended in water and extracted with methylene chloride. The extract was dried over anhydrous potassium carbonate and concentrated in vacuo. The residue was chromatographed on silica gel (200 g.) with 2% triethylamine-3% methanol-95% ethyl acetate (by volume). The product thus obtained was crystallized from methanol-ethyl acetate to give 0.83 g. (26%) of 1-methyl-8-nitro-6-phenyl-4H-s-triazolo[4,3-a][1,4]benzodiazepine of melting point 233°–234° C. The analytical sample prepared by recrystallizing this material from methanol-ethyl acetate had a melting point of 231.5°–232.5° C. The ultraviolet spectrum (ethanol) had end absorption λ max. 226 (ε = 21,500) and 259 mμ(ε = 18,850).

Anal. Calcd. for $C_{17}N_{13}N_5O_2$: C, 63.94; H, 4.10; N, 21.93. Found: C, 64.05; H, 3.85; N, 21.76.

EXAMPLE 13

Ethyl 8-chloro-6-phenyl-4H-s-triazolo[4,3-a]-[1,4]benzodiazepine-1-carboxylate

A mixture of 7-chloro-1,3-dihydro-5-phenyl-2H-1,4-benzodiazepine-2-thione (1.95 g.; 0.0068 mole), monoethyl oxalate hydrazide (2.7 g.; 0.0204 mole) and 1-butanol (50 ml.) was refluxed under nitrogen for 7 hours and concentrated in vacuo. The residue was suspended in water and extracted with methylene chloride. The extract was dried over anhydrous potassium carbonate and concentrated. The residue was chromatographed on silica gel (200 g.) with 60% ethyl acetate-40% Skellysolve B hexanes (by volume); 100-ml. fractions were collected. Fractions 36–60 were concentrated and the residue was crystallized from ethyl acetate-Skellysolve B hexanes to give 0.41 g. of ethyl 8-chloro-6-phenyl-4H-s-triazolo[4,3-a][1,4]benzodiazepine-1-carboxylate of melting point 234°–235.5° C. (dec.). The analytical sample was prepared by recrystallizing this material from ethyl acetate-Skellysolve B hexanes and had a melting point of 234°–235° C. (dec.). The ultraviolet spectrum (ethanol) had end absorption and inflections 223 (ε = 28,900), 250 (ε = 19,100) and 290 mμ(ε = 3,150).

Anal. Calcd. for $C_{19}H_{15}ClN_4O_2$: C, 62.21; H, 4.12; Cl, 9.67; N, 15.28. Found: C, 62.32; H, 4.02; Cl, 9.61; N, 15.14.

EXAMPLE 14

8-Chloro-1-methyl-6-(o-chlorophenyl)-4H-s-triazolo[4,3-a][1,4]benzodiazepine

A mixture of 1.0 g. (0.0031 mole) of 7-chloro-1,3-dihydro-5-(o-chlorophenyl)-2H-1,4-benzodiazepine-2-thione, 0.8 g. (0.0108 mole) of acetic acid hydrazide and 40 ml. of 1-butanol was heated at reflux temperature under nitrogen for 24 hours. During the first 5 hours the nitrogen was slowly bubbled through the solution. After cooling and removing the solvent in vacuo, the product was well mixed with water and collected on a filter, giving 0.9 g. of orange solid, melting point 210°–212° C. This was heated under nitrogen in an oil bath at 250° C. and then cooled. The solid was crystallized from ethyl acetate, giving 0.5 g. of tan solid of melting point 215°–216° C. (dec.). This was dissolved in 25 ml. of 2-propanol, filtered, concentrated to 10 ml. and cooled, yielding 0.46 g. (43%) of tan, crystalline 8-chloro-1-methyl-6-(o-chlorophenyl)-4H-s-triazolo[4,3-a][1,4]benzodiazepine of melting point 223°–225° C.

Anal. Calcd. for $C_{17}H_{12}Cl_2N_4$: C, 59.49; H, 3.52; Cl, 20.66; N, 16.32. Found: C, 59.55; H, 3.78; Cl, 20.72; N, 16.24.

EXAMPLE 15

8-Ethyl-1-phenyl-6-(o-chlorophenyl)-4H-s-triazolo-[4,3-a][1,4]benzodiazepine

In the manner given in Example 2, 7-ethyl-1,3-dihydro-5-(o-chlorophenyl)-2H-1,4-benzodiazepine-2-thione is heated in ethanol with benzoic acid hydrazide and the resulting product heated to 250° C. to give 8-ethyl-1-phenyl-6-(o-chlorophenyl)-4H-s-triazolo[4,3-a][1,4]benzodiazepine.

EXAMPLE 16

7-Ethylthio-1-methyl-6-(o-bromophenyl)-4H-s-triazolo[4,3-a][1,4]benzodiazepine

In the manner given in Example 2, 6-ethylthio-1,3-dihydro-5-(o-bromophenyl)-2H-1,4-benzodiazepine-2-thione is heated in ethanol with acetic acid hydrazide and the resulting product heated to 250° C. to give 7-ethylthio-1-methyl-6-(o-bromophenyl)4H-s-triazolo[4,3-a][1,4]benzodiazepine.

EXAMPLE 17

10-Trifluoromethyl)-6-[p-(propionylamino)phenyl]-4H-s-triazolo[4,3-a][1,4]benzodiazepine In the manner given in Example 2, 9-(trifluoromethyl)-1,3-dihydro-5-[p-(propionylamino)phenyl]-2H-1,4-benzodiazepine-2-thione is heated in ethanol with formic acid hydrazide and the resulting product heated to 250° C. to give 10-(trifluoromethyl)-6-[p-(propionylamino)pheyl]-4H-s-triazolo[4,3-a][1,4]benzodiazepine.

EXAMPLE 18

7-Ethylthio-1-ethyl-6-(o-bromophenyl)-4H-s-triazolo[4,3-a][1,4]benzodiazepine In the manner given in Example 2, 6-ethylthio-1,3-dihydro-5-(o-bromophenyl)-2H-1,4-benzodiazepine-2-thione is heated in ethanol with propionic acid hydrazide and the resulting product heated to 250° C. to give 7-ethylthio-1-ethyl-6-(o-bromophenyl)-4H-s-triazolo[4,3-a][1,4]benzodiazepine.

EXAMPLE 19

9-Propoxy-8-bromo-1-benzyl-6-[m-(ethylsulfinyl)phenyl]-4H-s-triazolo[4,3-a][1,4]benzodiazepine In the manner given in Example 2, 8-propoxy-7-bromo-1,3-dihydro-5-[m-(ethylsulfinyl)phenyl]-2H-1,4-benzodiazepine-2-thione is heated in ethanol with phenylacetic acid hydrazide and the resulting product heated to 250° C. to give 9-propoxy-8-bromo-1-benzyl-6-[m-(ethylsulfinyl)phenyl]-4H-s-triazolo-[4,3-a][1,4]benzodiazepine.

EXAMPLE 20

10-(Dipropylamino)-7-methyl-1-isopropyl-6-[m-(propylsulfonyl)phenyl]-4H-s-triazolo[4,3-a][1,4]benzodiazepine In the manner given in Example 2, 9-(dipropylamino)-6-methyl-1,3-dihydro-5-[m-(propylsulfonyl)phenyl]-2H-1,4-benzodiazepine-2-thione is heated in 1-propanol with isobutyric acid hydrazide and the resulting product heated to 250° C. to give 10-(dipropylamino)-7-methyl-1-isopropyl-6-[m-(propylsulfonyl)phenyl]-4H-s-triazolo-[4,3-a][1,4]benzodiazepine.

EXAMPLE 21

9-Cyano-1-propyl-6-[p-trifluoromethyl)phenyl]-4H-s-triazolo[4,3-a][1,4]benzodiazepine In the manner given in Example 2, 8-cyano-1,3-dihydro-5-[p-(trifluoromethyl)phenyl]-2H-1,4-benzodiazepine-2-thione is heated in ethanol with butyric acid hydrazide and the resulting product heated to 250° C. to give 9-cyano-1-propyl-6-[p-(trifluoromethyl)phenyl]-4H-s-triazolo[4,3-a][1,4]benzodiazepine.

EXAMPLE 22

9-Nitro-1-phenyl-6-(o-chlorophenyl)-4H-s-triazolo[4,3-a][1,4]benzodiazepine

In the manner given in Example 2, 8-nitro-1,3-dihydro-5-(o-chlorophenyl)-2H-1,4-benzodiazepine-2-thione is heated in ethanol with benzoic acid hydrazide and the resulting product heated to 250° C. to give 9-nitro-1-phenyl-6-(o-chlorophenyl)-4H-s-triazolo[4,3-a][1,4]benzodiazepine.

EXAMPLE 23

7,10-Dichloro-1-methyl-6-(p-isopropylphenyl)-4H-s-triazolo[4,3-a][1,4]benzodiazepine In the manner given in Example 2, 6,9-dichloro-1,3-dihydro-5-(p-isopropylphenyl)-2H-1,4-benzodiazepine-2-thione is heated in ethanol with acetic acid hydrazide and the resulting product heated to 250° C. to give 7,10-dichloro-1-methyl-6-(p-isopropylphenyl)-4H-s-triazolo[4,3-a][1,4]benzodiazepine.

EXAMPLE 24

4-Methyl-8-bromo-1-isopropyl-6-(o-fluorophenyl)-4H-s-triazolo[4,3-a][1,4]benzodiazepine In the manner given in Example 2, 3-methyl-7-bromo-1,3-dihydro-5-(o-fluorophenyl)-2H-1,4-benzodiazepine-2-thione is heated in ethanol with isobutyric acid hydrazide and the resulting product heated to 250° C. to give 4-methyl-8-bromo-1-isopropyl-6-(o-fluorophenyl)-4H-s-triazolo[4,3-a[]1,4]benzodiazepine.

EXAMPLE 25

1,4,7,9-Tetramethyl-6-(o-chlorophenyl)-4H-s-triazolo[4,3-a][1,4]benzodiazepine In the manner given in Example 2, 3,6,8-trimethyl-1,3-dihydro-5-(o-chlorophenyl)-2H-1,4-benzodiazepine-2-thione is heated in ethanol with acetic acid hydrazide and the resulting product heated to 250° C. to give 1,4,7,9-tetramethyl-6-(o-chlorophenyl)-4H-s-triazolo[4,3-a][1,4]benzodiazepine.

EXAMPLE 26

10-(Propylsulfonyl)-8-methyl-1-ethyl-6-phenyl-4H-s-triazolo[4,3-a[[1,4]benzodiazepine In the manner given in Example 2, 9-(propylsulfonyl)-7-methyl-1,3-dihydro-5-phenyl-2H-1,4-benzodiazepine-2-thione is heated in ethanol with propionic acid hydrazide and the resulting product heated to 250° C. to give 10-(propylsulfonyl)-8-methyl-1-ethyl-6-phenyl-4H-s-triazolo[4,3-a][1,4]benzodiazepine.

EXAMPLE 27

8-(Dimethylamino-6-phenyl-4H-s-triazolo[4,3-a][1,4]benzodiazepine

In the manner given in Example 2, 7-(dimethylamino)-1,3-dihydro-5-phenyl-2H-1,4-benzodiazepine-2-thione is heated in ethanol with formic acid hydrazide and the resulting product is heated to 250° C. to give 8-(dimethylamino)-6-phenyl-4H-s-triazolo[4,3-a][1,4]benzodiazepine.

EXAMPLE 28

7,10-Dichloro-1-phenyl-6-(p-isopropylphenyl)-4H-s-triazolo[4,3-a][1,4]benzodiazepine In the manner given in Example 2, 6,9-dichloro-1,3-dihydro-5-(p-isopropylphenyl)-2H-1,4-benzodiazepine-2-thione is heated in ethanol with benzoic acid hydrazide and the resulting product heated to 250° C. to give 7,10-dichloro-1-phenyl-6-(p-isopropylphenyl)-4H-s-triazolo[4,3-a][1,4]benzodiazepine.

EXAMPLE 29

7,9-Diethyl-1-benzyl-6-(m-ethylphenyl)-4H-s-triazolo[4,3-a][1,4]benzodiazepine In the manner given in Example 2, 6,8-diethyl-1,3-dihydro-5-(m-ethylphenyl)-2H-1,4-benzodiazepine-2-thione is heated in ethanol with phenylacetic acid hydrazide and the resulting product heated to 250° C. to give 7,9-diethyl-1-benzyl-6-(m-ethylphenyl)-4H-s-triazolo[4,3-a][1,4]benzodiazepine.

EXAMPLE 30

7-Nitro-1-methyl-6-(o-cyanophenyl)-4H-s-triazolo[4,3-a][1,4]benzodiazepine

In the manner given in Example 2, 6-nitro-1,3-dihydro-5-(o-cyanophenyl)-2H-1,4-benzodiazepine-2-thione is heated in ethanol with acetic acid hydrazide and the resulting product heated to 250° C. to give 7-nitro-1-methyl-6-(o-cyanophenyl)-4H-s-triazolo[4,3-a][1,4]benzodiazepine.

EXAMPLE 31

8-(Dipropylamino)-6-(o-nitrophenyl)-4H-s-triazolo[4,3-a][1,4]benzodiazepine

In the manner given in Example 2, 7-(dipropylamino)-1,3-dihydro-5-(o-nitrophenyl)-2H-1,4-benzodiazepine-2-thione is heated in ethanol with formic acid hydrazide and the resulting product heated to 250° C. to give 8-(dipropylamino)-6-(o-nitrophenyl)-4H-s-triazolo[4,3-a][1,4]benzodiazepine.

EXAMPLE 32

10-(Acetylamino)-1-ethyl-6-(p-cyanophenyl)-4H-s-triazolo[4,3-a][1,4]benzodiazepine In the manner given in Example 2, 9-acetylamino-1,3-dihydro-5-(p-cyanophenyl)-2H-1,4-benzodiazepine-2-thione is heated in ethanol with propionic acid hydrazide and the resulting product heated to 250° C. to give 10-(acetylamino)-1-ethyl-6-(p-cyanophenyl)-4H-s-triazolo[4,3-a][1,4]benzodiazepine.

EXAMPLE 33

Butyl 8-chloro-6-(m-nitrophenyl)-4H-s-triazolo[4,3-a][1,4]benzodiazepine-1-carboxylate In the manner given in Example 13, a mixture of 7-chloro-1,3-dihydro-5-(m-nitrophenyl)-2H-1,4-benzodiazepine-2-thione, monobutyl oxalate hydrazide and 1-butanol is refluxed under nitrogen for 7 hours to give butyl 8-chloro-6-(m-nitrophenyl)-4H-s-triazolo[4,3-a][1,4]benzodiazepine-1-carboxylate.

EXAMPLE 34

Methyl 9-fluoro-6-(2,4-dichlorophenyl)-4H-s-triazolo[4,3-a][1,4]benzodiazepine-1-carboxylate In the manner given in Example 13, a mixture of 8-fluoro-1,3-dihydro-5-(2,4-dichlorophenyl)-2H-1,4-benzodiazepine-2-thione, monomethyl oxalate hydrazide and 1-butanol is refluxed under nitrogen for 7 hours to give methyl 9-fluoro-6-(2,4-dichlorophenyl)-4H-s-triazolo[4,3-a][1,4]benzodiazepine-1-carboxylate.

EXAMPLE 35

8-Chloro-6-phenyl-4H-s-striazolo[4,3-a][1,4]benzodiazepine

A mixture of 5.74 g. (0.020 mole) of 7-chloro-1,3-dihydro-5-phenyl-2H-1,4-benzodiazepine-2-thione, 3.6 g. (0.060 mole) of formic acid hydrazide and 200 ml. of 1-butanol was refluxed for 3.75 hours with a slow stream of nitrogen bubbling through the mixture. The mixture was concentrated, the residue was suspended in water, and the suspension was filtered. The filter cake consisted principally of unchanged starting material. The filtrate was concentrated, ethyl acetate and Skellysolve B hexanes being added during the concentration, giving crude product (2.54 g.) of melting point 220.5°–225° C. Recrystallization of this material from ethyl acetate-Skellysolve B hexanes gave 8-chloro-6-phenyl-4H-s-triazolo[4,3-a][1,4]benzodiazepine of melting point 228°–229° C. The ultraviolet spectrum (ethanol) had end absorption λ max. 222 (ε = 40,950) and inflections at 245 (ε = 16,200) and 285 mμ(ε = 3,500).

Anal. Calcd. for $C_{16}H_{11}ClN_4$: C, 65.20; H, 3.76; Cl, 12.03; N, 19.01. Found: C, 65.26; H, 3.56; Cl, 12.30; N, 18.95.

In the manner given in the preceding examples, other 1,3-dihydro-5-phenyl-2H-1,4-benzodiazepine-2-thiones of formula I can be condensed with acid hydrazides II, as defined earlier, to give other new 6-phenyl-4H-s-triazolo[4,3-a][1,4]benzodiazepines. Representative compounds thus obtained include:
10-chloro-1-methyl-6-(m-isopropylphenyl)-4H-s-triazolo[4,3-a][1,4]benzodiazeipine;
9-(dipropylamino)-1-phenyl-6-[p-(propionylamino)-phenyl]-4H-s-triazolo[4,3-a][1,4]benzodiazepine;
8-(methylsulfinyl)-1-benzyl-6-(o-nitrophenyl)-4H-s-triazolo-[4,3-a][1,4]benzodiazepine;
7-(ethylsulfonyl)-1-propyl-6-(o-cyanophenyl)-4H-s-triazolo-[4,3-a][1,4]benzodiazepine;
4-propyl-1-isopropyl-6-[m-(methylthio)phenyl]-4H-s-triazolo-[4,3-a][1,4]benzodiazepine;
10-fluoro-7-chloro-1-ethyl-6-[p-(trifluoromethyl)-phenyl]-4H-s-triazolo[4,3-a][1,4]benzodiazepine;
7,9-diethoxy-1-methyl-6-(m-ethoxyphenyl)-4H-s-triazolo[4,3-a]-[1,4]benzodiazepine;
7-(propylthio)-6-(m-iodophenyl)-4H-s-triazolo[4,3-a][1,4]benzodiazepine;
8-(acetylamino)-6-p-iodophenyl-4H-s-triazolo[4,3-a][1,4]-benzodiazepine;
4-propyl-6-(o-iodophenyl)-4H-s-triazolo[4,3-a][1,4]benzodiazepine;
4-ethyl-1-methyl-6-[o-(ethylthio)phenyl]-4H-s-triazolo[4,3-a]-8 1,4]benzodiazepine;
4-methyl-7,10-dichloro-1-ethyl-6-(m-isopropoxyphenyl)-4H-s-triazolo[4,3-a][1,4]benzodiazepine;
9-(propionylamino)-1-propyl-6-[m-(propylthio)-phenyl]-4H-s-triazolo[4,3-a][1,4]benzodiazepine;
7-(diisopropylamino)-1-phenyl-6-[p-(dipropylamino)-phenyl]-4H-s-triazolo[4,3-a][1,4]benzodiazepine; and
4-isopropyl-7,9-diiodo-1-benzyl-6-phenyl-4H-s-triazolo[4,3-a][1,4]benzodiazepine;
8-chloro-1-methyl-6-(3,4-dimethylphenyl)-4H-s-triazolo[4,3-a][1,4]benzodiazepine;
6-(2-methyl-4-methoxyphenyl)-4H-s-triazolo[4,3-a][1,4]benzodiazepine;
8-methylthio-1-methyl-6-phenyl-4H-s-triazolo[4,3-a][1,4]benzodiazepine;
8-methoxy-1-methyl-6-phenyl-4H-s-triazolo[4,3-a][1,4]benzodiazepine; and the like.

I claim:
1. A 6-phenyl-4H-s-triazolo[4,3-a][1,4]benzodiazepine of the formula:

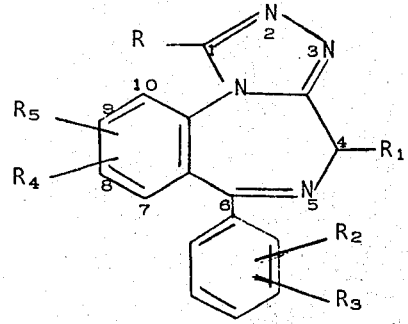

wherein R is selected from the group consisting of hydrogen, alkyl of 1 to 3 carbon atoms, inclusive, phenyl, and benzyl whwerein $R_1$ is selected from the group consisting of hydrogen and alkyl of 1 to 3 carbon atoms, inclusive; and wherein $R_2$, $R_3$, $R_4$, and $R_5$ are selected from the group consisting of hydrogen, alkyl of 1 to 3 carbon atoms, inclusive, halogen, nitro cyano, trifluoromethyl, and alkoxy, alkylthio, alkylsulfinyl, alkylsulfonyl, alkanoylamino and dialkylamino in which the carbon chain moieties are of 1 to 3 carbon atoms, inclusive, and their pharmacologically acceptable acid addition salts.

2. The compound of claim 1 wherein R is methyl, $R_1$, $R_2$, $R_3$, and $R_5$ are hydrogen and $R_4$ is 8-chloro and the compound is therefore 8-chloro-1-methyl-6-phenyl-4H-s-triazolo[4,3-a][1,4]benzodiazepine.

3. The compound of claim 1 wherein R is methyl, $R_1$ and $R_5$ are hydrogen, $R_2$ is 2-fluoro, $R_3$ is 6-fluoro, $R_4$ is 8-chloro, and the compound is therefore 8-chloro-1-methyl-6-(2,6-difluorophenyl)-4H-s-triazolo[4,3-a][1,4]benzodiazepine.

4. The compound of claim 1 wherein R is methyl, $R_1$, $R_2$ and $R_5$ are hydrogen, $R_3$ is o-fluoro, $R_4$ is 8-chloro and the compound is therefore 8-chloro-1-methyl-6-(o-fluorophenyl)-4H-s-triazolo[4,3-a][1,4]benzodiazepine.

5. The compound of claim 1 wherein R is methyl, $R_1$, $R_2$, $R_3$, $R_4$ and $R_5$ are hydrogen and the compound is therefore 1-methyl-6-phenyl-4H-s-triazolo[4,3-a][1,4]benzodiazepine.

6. The compound of claim 1 wherein R is propyl, $R_1$, $R_2$, $R_3$ and $R_5$ are hydrogen, $R_4$ is 8-chloro and the compound is therefore 8-chloro-1-propyl-6-phenyl-4H-s-triazolo[4,3-a][1,4]benzodiazepine.

7. The compound of claim 1 wherein R is phenyl, $R_1$, $R_2$, $R_3$ and $R_5$ are hydrogen, $R_4$ is 8-chloro and the compound is therefore 8-chloro-1,6-diphenyl-4H-s-triazolo[4,3-a][1,4]benzodiazepine.

8. The compound of claim 1 wherein R is benzyl, $R_1$, $R_2$, $R_3$ and $R_5$ are hydrogen, $R_4$ is 8-chloro and the compound is therefore 1-benzyl-8-chloro-6-phenyl-4H-s-triazolo[4,34,3-a][1,4]benzodiazepine.

9. The compound of claim 1 wherein R is ethyl, $R_1$, $R_2$, $R_3$ and $R_5$ are hydrogen, $R_4$ is 8-chloro and the compound is therefore 1-ethyl-8-chloro-6-phenyl-4H-s-triazolo[4,3-a][1,4]benzodiazepine.

10. The compound of claim 1 wherein R is methyl, $R_1$, $R_2$, $R_3$ and $R_5$ are hyrogen, $R_4$ is 8-trifluoromethyl and the compound is therefore 1-methyl-6-phenyl-8-(trifluoromethyl)-4H-s-triazolo[4,3-a][1,4]benzodiazepine.

11. The compound of claim 1 wherein R is methyl, $R_1$, $R_2$, $R_3$ and $R_5$ are hydrogen, $R_4$ is 8-nitro and the compound is therefore 1-methyl-8-nitro-6-phenyl-4H-s-triazolo[4,3-a][1,4]benzodiazepine.

12. The compound of claim 1 wherein R is methyl, $R_1$, $R_2$ and $R_5$ are hydrogen, $R_3$ is o-chloro, $R_4$ is 8-chloro and the compound is therefore 8-chloro-1-methyl-6-(o-chlorophenyl)-4H-s-triazolo[4,3-a][1,4]benzodiazepine.

13. The compound of claim 1 wherein R, $R_1$, $R_2$, $R_3$ and $R_5$ are hydrogen, $R_4$ is 8-chloro and the compound is therefore 8-chloro-6-phenyl-4H-s-triazolo[4,3-a][1,4]benzodiazepine.

14. The compound of claim 1 wherein R is methyl, $R_1$, $R_2$, $R_3$ and $R_5$ are hydrogen and $R_4$ is 8-methylthio and the compound is therefore 8-methylthio-1-methyl-6-phenyl-4H-s-triazolo[4,3-a][1,4]benzodiazepine.

15. The compound of claim 1 wherein R is methyl, $R_1$, $R_2$, $R_3$ and $R_5$ are hydrogen and $R_4$ is 8-methoxy and the compound is therefore 8-methoxy-1-6-phenyl-4H-s-triazolo[4,3-a][1,4]benzodiazepine.

* * * * *

UNITED STATES PATENT AND TRADEMARK OFFICE

CERTIFICATE EXTENDING PATENT TERM
UNDER 35 U.S.C. 156

Patent No.    :  3,987,052

Dated         :  October 19, 1976

Inventor(s)   :  Jackson B. Hester, Jr.

Patent Owner  :  The Upjohn Company

This is to certify that there has been presented to the

COMMISSIONER OF PATENTS AND TRADEMARKS an application under 35 U.S.C. 156 for an extension of the
patent term. Since it appears that the requirements of the law
have been met, this certificate extends the term of the patent
for the period of

2 YEARS with all rights pertaining thereto as provided by
35 U.S.C. 156 (b).

I have caused the seal of the Patent
and Trademark Office to be affixed
this 30th day of December, 1991.

Harry F. Manbeck, Jr.
Assistant Secretary and Commissioner
  of Patents and Trademarks